United States Patent [19]
Wu et al.

[11] Patent Number: 6,090,741
[45] Date of Patent: Jul. 18, 2000

[54] CATALYST COMBINATION AND PROCESS FOR THE LOW-TEMPERATURE CO-PRODUCTION OF METHANOL AND METHYL FORMATE IN LIQUID PHASE

[75] Inventors: Yutang Wu; Shizhong Luo; Xingquan Liu; Wenkai Chen; Chaoxia Jia; Shunfen Li; Zuolong Yu, all of Chengdu, China

[73] Assignee: Chengdu Institute of Organic Chemisty, Chinese Academy of Sciences, Chengdu, China

[21] Appl. No.: 09/145,735

[22] Filed: Sep. 2, 1998

[30] Foreign Application Priority Data

Sep. 2, 1997 [CN] China ................. 97 1 07662

[51] Int. Cl.$^7$ ..................................... B01J 31/00
[52] U.S. Cl. ........................ 502/171; 502/150; 502/151; 502/172
[58] Field of Search ..................... 502/150, 151, 502/152, 154, 156, 157, 171, 172

[56] References Cited

U.S. PATENT DOCUMENTS

| | | | |
|---|---|---|---|
| 4,731,386 | 3/1988 | Onsager | 518/700 |
| 5,221,652 | 6/1993 | Tierney et al. | 502/170 |
| 5,384,335 | 1/1995 | Tierney et al. | 518/700 |
| 5,385,949 | 1/1995 | Tierney et al. | 518/700 |

*Primary Examiner*—Elizabeth D. Wood
*Attorney, Agent, or Firm*—Schwegman, Lundberg, Woessner & Kluth, P.A.

[57] ABSTRACT

The present invention relates to a novel catalyst combination and a novel process for the synthesis of methanol and methyl formate (MF), and more specifically to the production of methanol and MF by contacting syngas under relatively mild conditions in a slurry phase with the novel catalyst combination comprising unreduced copper chromite prepared using specifical method, alkali alcoholates, a nonionics and a non-polar solvent. The nonionics, for example, $C_8H_{17}$—$(C_6H_4)$—O—$(C_2H_4O)_nH$ (where n is between 4 and 60) is used in the amount that is at least 5 vol. % of the slurry (liquid reaction medium). And the non-polar solvent having a dielectricity constant between 2 and 3 at 20° C. is used in the amount that is at least 50 vol. % of the slurry. The present invention allows the synthesis of methanol and MF to occur in the temperature range of approximately 100–150° C., and the pressure range of 3–8 MPa. The process produces methanol and MF with up to 95% syngas conversion per pass and up to 99% selectivity to methanol and MF. Very small amount of water, carbon dioxide and dimethyl ether is also produced. A space-time-yield of 88.3 gms./L/h is achieved when using a continuous stirring tank reactor (CSTR). A tubular slurry reactor of 10 liter volume without any mechanical agitator has been successfully used. The present catalyst combination also is capable of tolerating fluctuations in the $H_2$/CO ratio without major deleterious effect on the reaction rate. Furthermore, carbon dioxide and water are also tolerated without substantial catalyst deactivation.

9 Claims, No Drawings

CATALYST COMBINATION AND PROCESS FOR THE LOW-TEMPERATURE CO-PRODUCTION OF METHANOL AND METHYL FORMATE IN LIQUID PHASE

FIELD OF THE INVENTION

The present invention relates to a novel route for synthesizing methanol and methyl formate. More particularly, to the production of methanol and methyl formate using a catalyst combination comprising unreduced copper chromite, alkali alcoholate, a nonionics and a non-polar solvent.

BACKGROUND OF THE INVENTION

Methanol or methyl alcohol has industrially been produced for many decades. Its characteristic of burning without emitting pollutant substances such as $NO_x$, $SO_x$ and dust when used in steam generators or gas turbines, and its property of considerably reducing CO emission when used in mixture with gasoline, make methanol an ecological energy carrier.

Methanol used as an energy carrier also has a strategic importance in that it enable coal to be economically utilized as a cleaner fuel.

The crude product of the present process is a mixture of methanol and methyl formate which has the better burning performances and is cheaper compared to a single methanol. These characteristics make the crude product of the present process a very good energy carrier.

Moreover, methanol is an important chemical precursor. It is widely used in the manufacture of formaldehyde, chloromethans, acetic acid, acetic anhydride, methyl formate and dimethyl ether. Methanol also finds increasing use as an octane booster for gasoline by direct blending or as a raw material for methyl tert-butyl ether(MTBE) and for fuel cell application. Furthermore, there are the exciting discoveries that methanol can be converted to high octane gasoline (Mobil methanol-to-gasoline process) and olefins(UOP/Hydro methanol-to-olefins process).

All the industrial methods for producing methanol are very similar to each other and are based on two fundamental stages namely a first stage in which the raw material is converted into synthesis gas ($CO/H_2/CO_2$ mixture) and a second stage in which the $CO/H_2/CO_2$ mixture is converted into methanol with heterogeneous gaseous phase catalysis. The industrial operating conditions for latest generation copper catalysts are a pressure of 5–10 MPa, a temperature of 230–270° C. and an $(H_2—CO_2)/(CO+CO_2)$ of 5/1–8/1(by volume).

The relatively low conversion per pass and the consequent need to maintain a low inert gas ($N_2$, CH4 etc.) content in synthesis gas are the main limitation of current technology.

Catalyst systems operating under very mild temperature and pressure conditions (90–150° C., 1–5 MPa, respectively) have recently been developed. With these it is possible to obtain a very high CO conversion of greater than 90% per pass, to thus well overcome the main limitation of current technology. Many of these catalytic systems use nickel as the catalyst metal catalyst. All these systems have however the drawback of forming nickel carbonyl, a very toxic substance, under reaction conditions. A promising alternate metal is copper which does not form highly toxic substances under the low-temperature synthesis conditions. Furthermore when using copper as the catalyst metal, more methyl formate can be obtained.

Recently, methyl formate has been considered as a building block in the synthesis of various chemicals from syngas. An integrated chemical industry complex involving methyl formate could come into existence in the future. The number of reactions that convert methyl formate to other chemicals is large. In particular, the synthesis of large volume chemicals such as acetic acid, ethylene glycol and methyl methacrylate(MMA) deserve serious consideration. Compared to the conventional synthesis from syngas, the methyl formate routes usually require much milder reaction conditions, for example, in the process for producing acetic acid by the isomerization of methyl formate.

For manufacturing the large tonnage of commodity chemicals, it is necessary that methyl formate should be produced at much lower cost than that of the methanol carbonylation process.

Evidence showing that the low-temperature synthesis reaction can occur at 200° C., and 15–25 MPa with sodium carbonate or sodium formate in combination with a copper-chromium-calcium catalyst was provided.

Aker Engineering, in Petrol Engineering, reported a two-component liquid phase catalytic system to convent syngas to mixture of methanol and methyl formate in a single reactor. The process was reported to operate typically at 110° C. and 0.5 MPa. The report disclosed the use of only alkali and/or alkaline earth alkoxides(alcoholates) as the carbonylation catalyst with copper chromite as the hydrogenolysis catalyst. The report emphasized the need to eliminate all $CO_2$, $H_2O$ and sulfur compounds from the inlet syngas.

Similarly, U.S. Pat. No. 4,731,386 discloses preparation of methanol from syngas in a liquid reaction mixture in the presence of a catalyst system consisting of an alkali alcoholate and a heterogeneous copper catalyst. It was found that the addition of a non-polar organic solvent having weak cation solvating properties in the liquid phase, otherwise, consisting of methanol and methyl formate, substantially increased the catalytic activity of catalyst systems consisting of an alkali metal alcoholate and a heterogeneous copper catalyst.

More recently, U.S. Pat. No. 5,384,335 discloses a low-temperature process for the synthesis of methanol from syngas under relatively mild conditions in a slurry phase reactor with a catalyst combination comprising reduced copper chromite and basic alkali salts or alkaline earth salts. The invention allows the synthesis of methanol to occur in the temperature range of approximately 100°–160° C., and the pressure range of 4.0–6.5 MPa. The process produces methanol with up to 90% syngas conversion per pass and up to 95% methanol selectivity. The only major by-product is a small amount of methyl formate. Although the catalytic system of the U.S. Patent shows interesting characteristics such as its capacity to produce methanol by using the basic alkali salts or alkaline earth salts as a catalytic component under relatively mild reaction conditions, it has the limitation of low productivity, this being a important limitation from the applied viewpoint. In particular, the low-temperature($\leq 120°$ C.)activity of the catalytic system of the U.S. Patent is very low. Therefore the selectivity to methyl formate is also low when using the catalyst combination.

The object of present invention is to overcome the disadvantages in prior art, namely the high temperatures needed to synthesize methanol via the conventional gas-phase process using the copper-zinc catalysts and the low activity of using commercially available copper chromite as the catalyst component and to provide a high-activity copper catalyst and a highly efficient catalyst combination for the low-temperature co-production of methanol and methyl formate which enable the synthesis of methanol and methyl formate under mild temperatures while can be achieved high syngas conversion per pass and high productivity of methanol and methyl formate.

SUMMARY OF THE INVENTION

The present invention relates to a novel catalyst combination and a novel process for the synthesis of methanol and methyl formate (MF), and specifically specifical to the production of methanol and MF by contacting syngas under relatively mild conditions in a slurry phase with the novel catalyst combination comprising unreduced copper chromite prepared using specifically method, alkali alcoholates, a nonionics and a non-polar solvent. The nonionics, for example, $C_8H_{17}$—$(C_6H_4)$—O—$(C_2H_4O)_nH$ (where n is between 4 and 60) is used in the amount that is at least 5 vol. % of the slurry (liquid reaction medium). And the non-polar solvent having a dielectricity constant between 2 and 3 at 20° C. is used in the amount that is at least 50 vol. % of the slurry. The present invention allows the synthesis of methanol and MF to occur in the temperature range of approximately 100–150° C., and the pressure range of 3–8 MPa. The process produces methanol and MF with up to 95% syngas conversion per pass and up to 99% selectivity to methanol and MF. Very small amount of water, carbon dioxide and dimethyl ether is also produced. A space-time-yield of 88.3 gms./L/h is achieved when using a continuous stirring tank reactor(CSTR). A tubular slurry reactor of 10 liter volume without any mechanical agitator has been successfully used. The present catalyst combination also is capable of tolerating fluctuations in the $H_2/CO$ ratio without major deleterious effect on the reaction rate. Furthermore, carbon dioxide and water are also tolerated without substantial catalyst deactivation.

DETAILED DESCRIPTION OF THE PREFERRED EMBODIMENT OF THE INVENTION

The present invention relates to a novel route for the co-production of methanol and methyl formate from syngas using a novel catalyst combination or system comprising a copper chromite catalyst prepared by ourselves using special method of copper ammonium complex solution, alkali alcoholates, a nonionics and a non-polar solvent. It is known to produce "copper chromite" catalysts by calcination of a chemical compound with an approximate composition $Cu(OH)(NH_4)CrO_4$ in the presence of air at a temperature of approximately 350° C. and subsequent reduction of the product with hydrogen. The copper chromite catalysts of said kind may be utilized in the process, but according to the present invention, it proved especially suitable to use a special Cu—Cr oxide catalyst that is prepared by ourselves using the method of copper ammonium complex solution. The complex solution was prepared by mixturing 1M solution of copper nitrate and concentrated ammonium water. And then 1M solution of ammonium dichromate was dropped to the above complex solution. The filter cake obtained was dried for 15–20 hours in the range of 105–120° C., and then pulverized, thermally decomposed at 300–350° C. in a nitrogen, argon or helium flow for 2–4 hours. The resultant black powder which was directly used in the low-temperature synthesis reaction of the present invention without ordinary hydrogen reduction is called as CuCatE. Suitable alkali metals in alkali alcoholate include sodium, potassium and cesium. Suitable alcohols include methanol, ethanol and the other alcohols. Methanol is preferable. The nonionics, for example, $C_8H_{17}$—$(C_6H_4)$—O—$(C_2H_4O)_nH$ (where n is between 4 and 60) is used in the amount that is at least 5 vol. % of the liquid reaction medium (slurry). And the non-polar solvent which has a dielectricity constant between 2 and 3 at 20° C., such as xylene, dioxane, decalin etc., is used in the amount that is at least 50 vol. % of the liquid reaction medium.

The catalyst system of the present invention has the ability to tolerate the fluctuations in the $H_2/CO$ ratio without a major deleterious effect on the reaction rate. Almost no change in the reaction rate is observed in the $H_2/CO$ ratio range of 1.5–2.2:1. The present synthesis route thus enable the use of a wide range of $H_2/CO$ ratios. The $H_2/CO$ ratio can range from 0.5:1 to 3:1. Preferably, the $H_2/CO$ ratio ranges from 1.5–1.8.

Moreover, carbon dioxide in the inlet gas can also be tolerated. Experiments with an inlet syngas containing 0.1–0.3 v/v % $CO_2$ and up to 0.5% $O_2$ were run successfully.

Similarly, the presence of water can also be tolerated by the present catalysts system. A water concentration of 0.2–0.3% in the liquid phase does not seriously affects the reaction rate. The water gas shift reaction can easily be controlled to keep the water concentration within the acceptable range. However, it is preferable that the reactants should be as dry as possible.

The copper content of copper chromite catalyst is preferably in the range of 40–60%, Cu/Cr mole ratio in copper chromite catalyst is preferably in the range of 1.2:1 to 0.8:1. The reaction can be carried out in a continuous, semi-continuous or periodical manner at temperatures between approximately 100–160° C. and pressures preferably between approximately 3–8 MPa. The feed velocity at which the process is carried out is preferably in the range of 7–440 NL/h based on the different reaction volume. The copper chromite is preferably present in an amount of about 2 to 20 wt. % of the slurry. The alkali alcoholate is preferably present in an amount of about 2 to 30 wt. % of the slurry. Although pure methanol can be used as the solvent, a mixture of methanol and a non-polar organic compound is preferably used as the solvent for the synthesis reaction. The solvents can considerably increase the reaction rate, which include xylene, dioxane and decalin.

The methanol produced via this invention may be formed through a methyl formate intermediate or, more possibly, through a catalytic surface complex formed by interacting between copper chromite and alkali alcoholate. Similarly, methyl formate produced via this invention may be formed through the surface complex because it was found that there is a strong synergism between the carbonylation and the hydrogenolysis. When using the catalyst combinations of the present invention, overall reaction rate is hundred times higher than that of the individual hydrogenolysis of methyl formate under the same reaction conditions, which makes it possible that up to 95% syngas conversions and 99.6% selectivity to methanol and methyl formate can be obtained. The high per pass conversion of syngas eliminates or greatly reduces the necessity of the recycle. The syngas conversion per pass and selectivity to methanol and methyl formate obtained with the present catalyst combinations are comparable to those currently achieved by the industrial synthesis of methanol at temperatures of approximately 250° C. It should be emphatically noted that the space-time-yield (reactor productivity) of up to 88.3 gms./L/h at 110° C. has been reached using the catalyst combination of the present invention, which is very valuable for the commercialization of the present process.

The raw product of the present invention is basically consisted of methanol and methyl formate. Other impurities include water, $CO_2$ and dimethyl ether. Other oxygenated products or higher alcohols are produced, at most in trace quantities.

Low deactivation rates for the catalyst combinations of the present invention were obtained, thus ensuring continued catalyst activity. In the present invention, a novel unreduced catalyst combination was directly used for the synthesis reaction. By using the unreduced catalyst combination prepared by ourselves, much higher catalytic activity was obtained as compared with the reduced one.

The present process has several advantages over the industrial synthesis process of methanol and methyl formate, including:

1. Methanol can be manufactured by the present process at milder conditions of temperature of 100–160° C., and pressure of 4–8 MPa;
2. Up to 95% syngas conversion per pass can be obtained, resulting in very low recycle ratios;
3. Methyl formate, as a co-product of the present process, is directly synthesized using syngas without the need of water-free methanol and pure carbon monoxide;
4. Methanol synthesis can be achieved without using $CO_2$, resulting in the full use of hydrogen for synthesizing methanol and methyl formate;
5. The catalyst combination can tolerate fluctuations in the $H_2$:CO ratio effectively;
6. The liquid phase slurry synthesis of the present invention provides effective temperature control with rates comparable to the processes now operated commercially using copper/zinc oxide catalysts;
7. A tubular reactor of 10 liter volume which is much simpler in construction than that used commercially was successfully applied for the present invention.

EXAMPLES

Example 1

In Table 1, the reaction rate obtained using the present process is compared with those obtained with three prior art systems producing methanol.

TABLE 1

| Process | Type of Cu Catalyst Used and Reactor | Pressure (Mpa) | Temp. (° C.) | Rate of MeOH Production, gmole/h/kg |
|---|---|---|---|---|
| ICI | Cu—ZnO/$Al_2O_3$, Fixed Bed | 5.00 | 230 | 16.7 |
| LaPorte | Cu—ZnO/$Al_2O_3$, Slurry, Autoclave | 5.21 | 250 | 15.2 |
| U.S.P. 5,384,335 (1995) | Cu—Cr catalyst Commerically Used, Slurry Bed | 6.30 | 150 | 21.2 |
| Present Invention | CuCatE, Slurry Bed | 4.60 | 110 | 96.3 |

As seen from Table 1, the present process gives much higher rate at a significantly lower temperature (110° C., only) than that obtained by prior arts. The rate presented in Table 1 for the present invention is for a catalyst combination comprising 4 gms CuCatE and 7.6 gms. sodium methoxide in 170 ml xylene plus 30 ml methanol. The CO conversion per pass for this catalyst combination was 92.8% in a continuous stirring tank reactor(CSTR).

The advantageous features of the present catalyst combination are further described by the following examples.

Example 2

A solution of copper ammonium complex having pH=11 was prepared by mixturing 1M solution of copper nitrate and concentrated ammonia water. And then 1M solution of ammonium dichromate (pH=4) was dropped to the above solution of copper ammonium complex under stirring. After half of 1M solution of ammonium dichromate was dropped in the above complex solution, pH of the resultant solution was adjusted to 6 by addition of concentrated nitric acid, and then the remainder of ammonium dichromate solution was continuously dropped up. During the whole operation time, the solution temperature was kept at approximately 50° C. After finishing up the solution adding operation, the reaction mixture was aged for 3 hours under stirring at 50° C., and then filtered. And the precipitate obtained was washed with water until $NO_3^-$ in the solution can not be examined. The filter cake was dried for 16 hours at 120° C., and then pulverized, thermally decomposed at 300–350° C. in a nitrogen flow for 3 hours. The resultant black powder which was directly used in the synthesis reaction of the present invention without ordinary hydrogen reduction is called as CuCatE.

Example 3

Copper ammonium chromate, $Cu(OH)NH_4CrO_4$, was prepared by Adkin's method by adding a solution of copper nitrate to a solution of ammonium dichromate in water and at the same time adjusting the PH of the solvent to fall within the range 5.8 to 6.0 by addition of concentrated ammonia water. The precipitate was filtered from the mixture and washed with water. Then the product was dried at 105° C. for 16 hours, crushed to a fine powder and then dried for 20 hour at the same temperature. In order to obtain an active copper catalyst, the copper ammonium chromate was thermally decomposed in an inert nitrogen at 305° C. for 2 hours. The copper chromite catalyst prepared according to the above procedure is called CuCatA, that is, an improved Adkin's catalyst.

Example 4

Syngas having an inlet composition of 63.5% $H_2$, 31.5% CO, 0.3% $CO_2$ and 0.5% $O_2$ was fed to a 500 ml stainless steel autoclave charged with 4 gms copper chromite (CuCatA and CuCatE respectively), 6.1 gms sodium methoxide, 30 ml methanol and 170 ml xylene. The above catalyst combinations were not reduced before coming into synthesis reaction. The reactor was pressurized to 4 MPa with the above syngas and the temperature was adjusted to 110° C. using a temperature controller. The stirring speed of the autoclave was kept at 500 rpm. After a reaction time of 4 hours, the liquid products obtained were analyzed with gas chromatography equipped with a thermal conductivity detector and FID. A methanol production rates of 52.8 and 80.5 gmole/kgcat/h were obtained for CuCatA and CuCatE respectively. The methanol production rates include methanol used for the formation of methyl formate. Neither of the Cu catalyst (A and E) was reduced with hydrogen before they were used for the low-temperature synthesis reaction of methanol and methyl formate. A liquid product composition of 80.6% methanol, 19.0% methyl formate, 0.3% water and traces of dimethyl ether and dissolved gases was obtained.

Example 5

The same experimental procedure as described in Example 4 was used. However, the CuCatA was reduced with hydrogen for 4 hours at temperatures between 200–230° C. in a separate tubular reactor before it was used in the synthesis of methanol and methyl formate. A methanol production rate of 10 gmole/kgcat/h (6.4 g/L/h) was obtained, which is 5 times lower than that obtained with the unreduced CuCatA(52.8 gmole/kgcat/h) under the same reaction conditions.

Example 6

The same experimental procedure as described in Example 4 was used. However, CuCatA used was reduced in the autoclave used for synthesis reaction as a slurry in methanol for 2 hours at 170° C. and 8 MPa hydrogen pressure. After the prereduction the CuCatA was washed 2–3 times with methanol to remove water and dried, and then used for synthesis reaction of methanol and methyl formate. A methanol production rate of 8.8 gmole/kgcat/h was obtained, which is 6 times lower than that obtained with unreduced CuCatA (52.3 gmole/kgcat/h) under the same reaction conditions.

Example 7

The same experimental procedure as described in Example 4 was used. Instead of the syngas having inlet composition of 63.5% $H_2$, 31.5% CO, a syngas having inlet composition of 47.3% $H_2$, 46.4% CO, 0.82% $O_2$ and 0.43% $CO_2$ (the rest $N_2$)was used. Copper chromite of the catalyst combination used is CuCatE unreduced. A methanol production rate of 70.6 gmole/kgcat/h was obtained, which is 1.14 times smaller than that obtained when using the syngas having $H_2$/CO ratio=2.

Example 8

The same experimental procedure as described in Example 4 was used. The effects of Cu/Cr ratio (mole) in copper chromite are illustrated in the present example, as shown in Table 2. The copper chromite catalyst used in Table 2 is CuCatE.

TABLE 2

| Cu/Cr(mole) | 0.8 | 1.0 | 1.2 |
|---|---|---|---|
| Rate of MeOH Production, gmole/kgcat./h | 77.3 | 80.5 | 70.8 |

Example 9

The same experimental procedure as described in Example 4 was used. The effects of the concentration of copper chromite (CuCatE) in the slurry used for the synthesis reaction are illustrated in the present example, as shown in Table 3.

TABLE 3

| [CuCat], g/L | 0 | 5.0 | 10.0 | 15.0 | 20.0 | 30.0 | 40.0 |
|---|---|---|---|---|---|---|---|
| Rate of MeOH Production, gmole/kgcat./h | 6.4 | 17.7 | 33.0 | 78.9 | 80.5 | 88.6 | 104.7 |

From the Table 3, it can be seen that the increase of the reaction concentrations of CuCatE in the reaction slurry results in the increase of methanol production rates, which is very important for the commercialization.

Example 10

The same experimental procedure as described in Example 4 was used. The effects of the concentration of sodium methoxide in the slurry are illustrated in the present example, as shown in Table 4. The concentration of CuCatE used in Table 4 is 20 g/L.

TABLE 4

| [MeONa], g/L | 2.1 | 10.2 | 15.2 | 30.5 | 61.0 |
|---|---|---|---|---|---|
| Rates of MeOH Production, gmole/kgcat/h | 22.5 | 45.1 | 66.8 | 80.5 | 80.5 |

From the Table 4, it can be seen that the concentration of sodium methoxide in the slurry must be higher than 20 g/L. In other words, the ratio (w/w) of copper chromite to sodium methoxide must be smaller than 1.

Example 11

The same experimental procedure as described in Example 4 was used. The effects of methanol concentration in xylene were considered, as shown in Table 5.

TABLE 5

| MeOH, v/v % | 15 | 28 | 60 | 75 | 90 |
|---|---|---|---|---|---|
| Rates of MeOH Production, gmole/kgcat/h | 80.5 | 58.8 | 56.4 | 57.2 | 48.3 |

Example 12

The same experimental procedure as described in Example 4 was used. The effects of reaction temperature were considered in the present Example, as shown in Table 6.

TABLE 6

| Reaction Temperature, ° C. | 80 | 100 | 110 | 120 | 130 | 150 |
|---|---|---|---|---|---|---|
| Rate of MeOH production, gmole/h/kgCuCatE | 49.1 | 73.3 | 80.5 | 87.7 | 87.7 | 63.6 |

Example 13

The effects of the reaction pressure were considered. The results obtained show that the production rates of methanol and methyl formate markedly increase with the increase of the reaction pressure in all the experiments.

Example 14

Reactions were carried out in a semicontinuous (gas continuous, liquid batch) manner by continuously bubbling syngas metered by an on-line mass flow controller into a 500 ml stainless steel autoclave equipped with magnetic stirrer as reactor in which the above copper chromite prepared by ourselves, sodium methoxide, 30 ml methanol and 170 ml xylene were charged. The stirring speed was kept at 500 rpm. The reactor was pressurized to reaction pressure, the pressure being controlled by a pressure regulator (YT-4). The gas effluent rate was measured by a calibrated wet test flow meter. Gas and liquid analysis was carried out at regular intervals using SC-3 gas chromatography. The methanol production rate and the selectivity to methanol and methyl formate were determined from the results of the GC analysis of liquid products. CO conversions per pass were determined from the GC analysis of gas feeds and products and their flows. None of the copper catalysts used for the present Example were reduced with hydrogen before coming into the synthesis reaction. The several typical experimental results obtained are shown in Table 7.

TABLE 7

| Reaction Temperature, °C. | CO Partial Pressure, MPa | MeONa/ CuCatE, w/w | CO Conversion Per Pass, % | STY, g/L/h | $S_{MF}$, w/w % | Run No. |
|---|---|---|---|---|---|---|
| 108 | 1.46 | 1.90 | 92.8 | 61.6 | 24.8 | 6-1&2 |
| 110 | 1.44 | 0.95 | 97.2 | 52.7 | 24.0 | 8-1&2 |
| 108** | 1.54 | 1.27 | 95.3 | 42.0 | 33.2 | 9-1&2 |
| 108 | 1.30 | 1.90 | 98.4 | 59.0 | 32.7 | 15-1&2 |
| 111 | 1.28 | 1.00 | 97.6 | 47.8 | 34.9 | 17-1 |

The experimental runs in Table 7 were performed for a period from 7 to 14 hours. As seen on Table 7, even higher space-time-yield (STY, reactor productivity) than those achieved in periodical operation manner (from Example 2 to Example 13) are obtained when the semicontinuous reactor charged with the catalyst combination based on unreduced copper catalysts was used. The highest methanol production rate of 96.3 gmole/kgcat/h (i.e.STY=61.6 g/L/h) is obtained with 92.8% CO conversion per pass. For all the experiments in the Table 7, methanol and methyl formate amount to 99.6% of the products, the others are 0.3% water and traces of dimethyl ether and dissolved gases.

Example 15

The same experimental procedure as described in Example 14 was used. The effects of the ratio of sodium methoxide to copper chromite on the rate of deactivation of the catalyst combinations used in the present invention were considered. The results obtained are shown in Table 8.

TABLE 8*

| Cu Catalyst No. | Loaded Weight of CuCat, g | MeONa/ CuCat, w/w | On-Stream Period, h | Co Conversion Per Pass, % | Run No |
|---|---|---|---|---|---|
| CuCatE-2' | 7.3 | 1.89 | 7.7 | 98.2 | Run 2-1 |
| | | | 14.7 | 94.5 | 2-2 |
| CuCatE-1 | 6.0 | 1.90 | 8.5 | ~100 | Run 15-1 |
| | | | 11.8 | 96.7 | 15-2 |
| CuCatE-1' | 8.0 | 0.95 | 8.5 | 97.2 | Run 8-1 |
| | | | 13.5 | 88.5 | 8-2 |
| | 6.0 | 1.27 | 5.5 | 95.3 | Run 9-1 |
| | | | 12.5 | 78.8 | 9-2 |

*Experimental conditions: 110° C.; 3.4–5.3 MPa, $P_{CO}$ = 1.09–1.66 MPa; Syngas Feed 18.0–21.6 NL/h; xylene plus methanol as solvent As seen from Table 8, the ratio of MeONa/CuCat (w/w) should be kept to be greater than 1.5 for the deactivation rate of the present catalyst combinations to be able to lower to very low value.

Example 16

The same experimental procedure as described in Example 14 was used. The effects of the solvents were considered, as shown in Table 9

TABLE 9*

| Solvent | Volume Loaded, ml | CO Conversion Per Pass, % | STY, g/L/h | Run No |
|---|---|---|---|---|
| Xylene | 170 | 95.3 | 44.5 | Run 9-1 |
| Dioxane | 170 | 94.5 | 43.8 | Run 10-1 |
| Decalin | 170 | 97.9 | 46.7 | Run 11-1 |

*Experimental Conditions: CuCatE-1, 6 g; MeONa/CuCatE (w/w) = 1; 110° C.; 4.22–4.53 MPa (Total); $H_2$/CO = 2.07

As seen from Table 9, the near results are obtained when using the three of the solvents.

Example 17

The same experimental procedure as described in Example 14 was used. The repeatability in preparing copper chromite and formulating catalyst components into the combinations was considered, as shown in Table 10. As seen from Table 10, the preparing repeatability of the copper catalysts and the catalyst combinations developed by our laboratory has been achieved. As is well known, it is very difficult to realize repeatable preparation of a complex catalyst system. However, it is very important for the commercialization of the catalyst system.

TABLE 10*

| Cu Catalyst No. | CO Conversion Per Pass, % | STY, g/L/h | Run No. |
|---|---|---|---|
| CuCatE-1 | 98.4 | 54.6 | Run 15-1 & 2 |
| CuCatE-1 | 97.6 | 49.7 | Run 17 |
| CuCatE-2 | ~100 | 52.4 | Run 18 & 19 |

*Experimental conditions: CuCat Loading 4–6 g; MeONa/CuCat = 1~2.13 (w/w); 110° C.; Total Pressure 3.39~4.70 MPa; $H_2$/CO = 1.7

Example 18

The same experimental procedure as described in Example 14 was used. The rate of deactivation of the catalyst combination based on CuCatE of the present invention was considered, as shown in Table 11.

TABLE 11*

| On-Stream Time, h | CO Conversion Per Pass, % | Impurity (in Feed Gas), v/v % | | Run No |
|---|---|---|---|---|
| | | $O_2$ | $CO_2$ | |
| 9.5 | 97.9 | 0.094 | 0.1 | Run 1-1 |
| 14.5 | 98.3 | 0.06 | 0.1 | 1-2 |
| 22.5 | 98.8 | | | 1-3 |
| 30.5 | 98.2 | | | 1-4 |

*Experimental Conditions: 102–107° C.; Total Pressure 4.9 MPa; $H_2$/CO = 1.74; Syngas Feed Flow 7.13–8.41 NL/h As seen from Table 11, during on-stream time of 30.5 hours, the very high CO conversion per pass (98%) remains unchanged under as low reaction temperature as 110° C.

Example 19

The same experimental procedure as described in Example 14 was used. However, a 1000 ml continuous stirred tank reactor (CSTR) was used as the synthesis reactor, and then the syngas having an inlet composition of 63.9% $H_2$, 34.4% CO, 1.3% $CH_4$ and 0.5% $N_2$ was used as feed gas. The CSTR was charged with 12 gms. CuCatE-1, 24.3 gms sodium methoxide, 90 ml methanol and 310 ml xylene. The other reaction conditions were 110° C., 4.25

MPa(total pressure) and syngas flow of 20 NL/h. During on-stream time of 8 hours, up to 94% syngas conversion per pass and 95% CO conversion per pass remained unchanged.

Example 20

Utilizing the same CSTR (1000 rpm), experimental conditions and experimental procedure as described in Example 19, except that the reactor was charged with 12 gms. CuCatE-1, 17 gms sodium methoxide, 60 ml methanol, 370 ml xylene and 40 ml OP-10. During on-stream time of 8.5 hours, up to 94% syngas conversion per pass and 95% CO conversion per pass remained unchanged.

Example 21

Utilizing the same CSTR (stirring speed=1000 rpm), experimental conditions and experimental procedure as described in Example 19, except that the reactor was charged with 40 gms. CuCatE-1, 40.5 gms sodium methoxide, 150 ml methanol and 250 ml xylene, and correspondingly the syngas flow of 77.8 NL/h was used. During on-stream time of 6.5 hours, up to 90.2% syngas conversion per pass and 92.4% CO conversion per pass remained unchanged. A space-time-yield (reactor productivity) of 88.3 gms methano /h/L was obtained. As well known, the high enough space-time-yield is very important for the process commercialization.

Example 22

Utilizing the same experimental procedure as described in Example 19, except that the reactor used was not a CSTR and the experimental scale is 10 times larger than the reactor used for Example 19. A tubular reactor without any mechanical agitator was used. The tubular reactor having 1.5 m in height and 0.093 m inside diameter was charged with 120 gms. unreduced CuCatE-1, 185 gms. sodium methoxide, 685 ml methanol, 3400 ml xylene and 400 ml OP-10 ($C_8H_{17}$—($C_6H_4$)—O—($C_2H_4O$)$_n$H, n=10). 440 NL per hour of purified syngas having an inlet composition of 63.9% $H_2$, 34.4% CO, 0.5% $N_2$ and 1.3% $CH_4$ were bubbled through a gas distributor to the reaction zone of the tubular reactor at 100° C., 4.8 MPa(total pressure). CO conversion per pass of up to 90.2% was obtained. The productivity of the tubular reactor is about 92.7% of the continuous stirring tank reactor under the same reaction conditions. The above results obtained in our laboratory are very important for the commercialization of the present invention because methanol and methyl format are both large volume commodity chemicals which can hardly be produced using CSTR.

Example 23

This Example is a control experiment in which the experimental procedure and conditions are the same as Example 22, but the OP-10 component is absent in catalyst combination. To a 10 l tubular reactor the same amounts of Cucat E-1, sodium methoxide, methanol and xylene as described in the Example 22 are added except OP-10, the nonionics. The results are: when the syngas flow rate is under the same condition as in Example 22(syngas feed flow of 440 NL/h), the CO conversion per pass is only 35%, the reactor productivity is only 38.8% of that in the Example 22.

What is claimed is:

1. A catalyst combination for co-producing methanol and methyl formate from syngas comprising carbon monoxide and hydrogen in a slurry or a liquid reaction medium, comprising copper chromite in an amount of about 2 to 20 wt. % of the slurry, alkali metal alcoholate in an amount of about 2 to 30 wt. % of the slurry, a non-ionic surface active agent in an amount of at least 5 vol. % of the slurry and a non-polar solvent in an amount of at least 50 vol. % of slurry.

2. The catalyst combination of claim 1 wherein the copper chromite is prepared by the following steps:

mixing 1 M solution of copper nitrate with concentrated ammonia water, resulting in a copper ammonium complex solution having pH of 10–12;

preparing a $Cu(OH)NH_4CrO_4$ precipitate by dropping ammonium dichromate solution into the above copper ammonium complex solution at temperature between 25–65° C. and at pH between 5.4–6.4 which is adjusted by adding concentrated nitric acid, and washing and filtering the precipitate, resulting in a filter cake;

drying the resultant filter cake at a temperature of 105–120° C. for 14–20 hours; and pulverizing and thermally decomposing the said filter cake at temperature between 300–350° C. in a nitrogen or argon atmosphere for 2–4 hours, thus the copper chromite is obtained.

3. The catalyst combination of claims 1 or 2 wherein the copper chromite contains copper in a range of 40–60 wt. % of the final catalyst composition.

4. The catalyst combination of claims 1 or 2 wherein the copper chromite comprises Cu and Cr in the mole ratio (Cu/Cr) of 1.2:1 to 0.8:1.

5. The catalyst combination of claims 1 or 2 wherein the alkali metal alcoholate is selected from the group consisting of potassium methoxide or sodium methoxide.

6. The catalyst combination of claim 1 or 2 wherein the non-ionic surface active agent is $C_8H_{17}$—($C_6H_4$)—O—($C_2H_4O$)$_n$H where n is between 4 and 60.

7. The catalyst combination of claim 1 or 2 wherein the non-polar solvent has a dielectricity constant of 2–3 at 20° C.

8. The catalyst combination of claim 1 or 2 wherein the non-polar solvent is dioxane, or, xylene or decalin.

9. The catalyst combination of claim 1 or 2 wherein the ratio of the alkali metal alcoholate/copper chromite (W/W) is $\geq 1$.

* * * * *

UNITED STATES PATENT AND TRADEMARK OFFICE
CERTIFICATE OF CORRECTION

PATENT NO.    : 6,090,741
DATED         : July 18, 2000
INVENTOR(S)   : Wu et al.

It is certified that error appears in the above-identified patent and that said Letters Patent is hereby corrected as shown below:

Column 1,
Line 64, after "metal" insert -- catalyst --.

Column 3,
Line 11, delete "specificial" and insert -- more --, therefor.

Column 12,
Line 53, delete "≧" and insert -- ≥ --, therefor.

Signed and Sealed this

Ninth Day of October, 2001

Attest:

NICHOLAS P. GODICI
Attesting Officer    Acting Director of the United States Patent and Trademark Office